United States Patent [19]

Casas-Perez

[11] Patent Number: 5,480,641
[45] Date of Patent: Jan. 2, 1996

[54] **FEED ADDITIVE WHICH CONSISTS OF WHEY AND *LACTOBACILLUS REUTERI* AND A METHOD OF DELIVERING *LACTOBACILLUS REUTERI* TO THE GASTROINTESTINAL TRACT**

[75] Inventor: Ivan A. Casas-Perez, Raleigh, N.C.

[73] Assignee: Biogaia AB, Stockholm, Sweden

[21] Appl. No.: 77,895

[22] Filed: Jun. 15, 1993

Related U.S. Application Data

[63] Continuation of Ser. No. 646,863, Jan. 28, 1991, abandoned, which is a continuation-in-part of Ser. No. 539,014, Jun. 15, 1990, abandoned.

[51] Int. Cl.$^6$ .............................. C12N 1/20; A61K 35/74; A23L 1/28
[52] U.S. Cl. ................. 424/93.45; 424/93.4; 435/252.9; 435/853; 426/61
[58] Field of Search ................................. 435/853, 252.9; 424/93 J, 93.45, 93.4; 426/61

[56] References Cited

U.S. PATENT DOCUMENTS

| | | | |
|---|---|---|---|
| 3,984,575 | 10/1976 | Farr | 426/2 |
| 3,988,440 | 10/1976 | Bogdanov | 424/115 |
| 4,518,696 | 5/1985 | Gehrman et al. | 435/253 |
| 4,591,499 | 5/1986 | Linn et al. | 424/93 |
| 4,689,226 | 8/1987 | Nurmi et al. | 424/93 |
| 4,946,791 | 8/1990 | Manfredi et al. | 435/252.9 |
| 4,980,164 | 12/1990 | Manfredi et al. | 424/93 |

FOREIGN PATENT DOCUMENTS 0130680  3/1985  Japan ....................................... 424/93

OTHER PUBLICATIONS

Food & Drug Administration Compliance Policy Guides, Chapt. 26 (May 2, 1988) pp. 1–4.
Alaeddinoglu et al, Enzyme Microb. Technol, 11(11) 1989, pp. 765–769 (Biosis Abstract).
Fayed et al, Egypt J. Food Sci, 14(2) 1986, pp. 313–322 (Biosis Abstract).
Mitchell et al, J. Diary Sci, 66(4) 1983, pp. 712–718 (Biosis Abstract).
Parkhurst et al, Poult Sci, 70 (Suppl. 1) 1991 p. 173.
Edens et al, Poult. Sci, 70 (Suppl. 1) 1991, p. 37.
Chung et al, Microbial Ecology of Health & Disease, vol. 2: (1989) p. 137–144.
Dobrogosz et al, "*Lactobacillus reuteri* and the Enteric Microbiota", pp. 283–292 (1989).

*Primary Examiner*—Marian C. Knode
*Assistant Examiner*—Susan M. Dadio
*Attorney, Agent, or Firm*—Olive & Olive

[57] ABSTRACT

A method of establishing direct feed microorganisms such as *Lactobacillus reuteri* in the gastrointestinal tract of avian organisms, in which the direct feed microorganisms are added to whey and fed in the form of pellets (compacted whey particles) to the organisms.

8 Claims, No Drawings

FEED ADDITIVE WHICH CONSISTS OF WHEY AND *LACTOBACILLUS REUTERI* AND A METHOD OF DELIVERING *LACTOBACILLUS REUTERI* TO THE GASTROINTESTINAL TRACT

This is a continuation of U.S. application Ser. No. 07/646,863, filed Jan. 28, 1991, now abandoned, which is a continuation-in-part of U.S. application Ser. No. 07/539,014, filed Jun. 15, 1990, now abandoned.

FIELD OF INVENTION

This invention relates to a new method for delivering viable microbial cells in animals' diets.

BACKGROUND INFORMATION

The terms "probiotics" is attributed to Parker (20) who defined them as "organisms and substances which contribute to intestinal balance" when used as dietary supplements. This publication and all other publications and patents cited herein are incorporated herein by reference. Later, Fuller (11) considered this definition to be too broad since, in addition to including cell cultures and microbial metabolites, it could encompass antibiotic preparations. More recently, a number of summaries have appeared in the literature describing the scientific basis for use of probiotics as intestinal inoculants for production animals (10, 26). It has been suggested that the term "probiotics" be replaced by the term "direct feed microorganisms," or DFM's (9).

The concept of adding viable, harmless lactic acid bacteria to the gastrointestinal tract as a dietary supplement was first appreciated by Metchnikoff (16) who viewed the consumption of yoghurt by Bulgarian peasants as conferring a long span of life. Some workers have claimed that the therapeutic value derived from ingestion of such fermented milk products is related to the viable bacteria present in these products (12, 27). Since Metchnikoff's early reports, several studies have shown the ability of lactobacilli, for example, to suppress coliform growth. Feeding viable Lactobacillus acidophilus cells to young dairy calves was shown to reduce the incidence of diarrhoea (3), and increase the numbers of lactobacilli and reduce coliform counts in feces (4). These findings contrast with those of others who were unable to demonstrate benefits from feeding either *Lactobacillus acidophilus* (8, 13) or milk cultured with *Lactobacillus acidophilus* or *Lactobacillus lactis* (17).

In a detailed study by Muralidhara et.al. (18), piglets given a *Lactobacillus lactis* concentrate for up to 8 weeks after birth showed a progressive decline in coliform counts in fecal samples. Scouring in these animals was negligible, but was evident in control pigs especially at weaning. Underdahl et al. (32) observed only mild diarrhoea lasting 2–4 days in gnotobiotic pigs inoculated with *Streptococcus faecium* prior to artificial *Escherichia coli* infection. In the same study, persistent diarrhoea occurred in pigs similarly infected with *Escherichia coli*, but without prophylactic treatment with the Streptococcus microorganism.

Probiotics (hereafter referred to as DFM's) are bacterial or yeast preparations that are administered orally or added to feeds. The most commonly used DFM's are strains of the lactic acid bacteria (LAB), particularly those classified in the following genera: Lactobacillus, Latcococcus, and Enterococcus. Included among these are the following species: *Lactobacillus acidophilus, Lactobacillus bulgaricus, Lactobacillus plantarum, Lactobacillus casei, Lactobacillus lactis, Latcococcus lactis, Latcococcus thermophilus, Latcococcus diacetylactis,* and *Enterococcus faecium*. Besides these LAB, some species of Bacillus (*Bacillus subtilis, Bacillus toyoi*) and yeasts and molds (*Saccharomyces cerevisiae, Aspergillus oryzae,* and *Torulopsis sp.*) are used as DFM's (10).

It is generally held that during periods of low resistance, such as stress, undesirable microorganisms are able to proliferate in the GI tract of animals, humans included. Maintaining a normal, healthy balance of microorganisms is deemed to be critical during such stressful periods (10). The concept underlying use of DFM's, therefore is that if sufficient numbers of an appropriate microorganism(s) are introduced into the intestinal tract (i) at times of stress and/or disease, (ii) at birth, or (iii) after antibiotic treatment (when minimal LAB are present), the negative consequences of the microbial imbalances can be minimized or overcome. Using such preparations of live, naturally occurring microorganisms helps restore and maintain the proper balance of beneficial microbes in the GI tract during times of stress, disease, and following antibiotic therapy (10). This concept, descriptions of proposed modes of action, and evidence for the efficacious uses of DFM's for all production animals are summarized in reviews by Fox (10), Sissons (26), and by various authors (22).

One of the major problems or limitations encountered in commercial scale application of DFM's to animals is (i) the availability of suitable delivery systems, and (ii) the ability to get the probiotic preparations to the animals as quickly as possible after birth. This is particularly true when pelletized feeds are used, as is the case in the poultry industry. The pelletization process generally includes one or more heating steps involving temperatures high enough to pasteurize or sterilize the feed components, thereby precluding incorporation of viable microorganisms into these feeds prior to pelletization.

The present invention describes novel methods and processes for overcoming some of these problems, by delivering viable DFM's in feed additives. The DFM used to develop these methods is *Lactobacillus reuteri*. This species was chosen because it has demonstrated efficacy as a DFM in poultry (21). Previous patent applications have been submitted relating to unique properties of the species. These applications are: PCT/US88/01423, filed Apr. 28, 1988 and published Nov. 3, 1988, claiming priority from U.S. Ser. No. 07/268,361 filed Sep. 19, 1988 which is a continuation-in-part of U.S. Ser. No. 07/102,830 filed Sep. 22, 1987 which is a continuation-in-part of U.S. Ser. No. 07/046,027 filed May 1, 1987; and U.S. Ser. No. 07/539,014 filed Jun. 15, 1990. The disclosure of these applications is incorporated herein by reference.

*Lactobacillus reuteri* is a species of lactic acid bacteria recognized since the turn of the century (19). Originally assigned different species names (e.g., *Lactobacillus fermentum* biotype II), it obtained distinct species status in 1980 and is registered in the 1988 edition of Bergey's manual (14, 15). It is found in foods, particularly dairy products and meats, but exists primarily in the GI tract of healthy animals, including humans (1, 6, 7, 14, 15, 23, 24, 25, 33).

*Lactobacillus reuteri* is the dominant heterofermentative Lactobacillus inhabiting the GI tract (23, 24, 25). It is a typical heterofermenter, converting sugars into acetic acid, ethanol, and $CO_2$ in addition to lactic acid which is the major endproduct of homofermentative metabolism carried out by species such as *Lactobacillus acidophilus* (31). It utilizes the phosphoketolase pathway for conversion of glucose to end-products. When glycerol, an alternate hydrogen acceptor, is present in the culture medium together with glucose or other utilizable carbon and energy sources (e.g., lactose), acetate rather than ethanol accumulates, and the glycerol is reduced to 1,3-propanediol via the metabolic intermediate, 3-hydroxypropionaldehyde (3-HPA). 3-HPA has been shown to have potent antimicrobial activity, and *Lactobacillus reuteri* appears to be unique among microorganisms examined to date in its ability to secrete this substance, termed reuterin, into the surrounding medium (2, 5, 7, 28, 29, 30, 31). This unique antimicrobial activity may play a role in competitive survival of this species in the gastrointestinal ecosystem, and/or its ability to regulate growth and activities of other microorganisms in this ecosystem (7). It is thus very important to establish this microorganism early in animals. It is therefore an object of the invention to provide a method for delivering DFM's, such as Lactobacillus, to avian species.

Other objects and advantages will be more fully apparent from the following disclosure and appended claims.

SUMMARY OF INVENTION

A dietary supplement is prepared containing viable cells of a DFM such as *Lactobacillus reuteri*, an oil and a cryoprotectant such as whey powder. The Lactobacillus cells may be coated on the surface of whey pellets or be contained in the pellets. As used herein, the word "pellet" means a compacted whey particle which may be of any size or shape that is ingestible by the animal to be fed the supplement.

Other aspects and features of the invention will be more fully apparent from the following disclosure and appended claims.

DETAILED DESCRIPTION OF THE INVENTION AND PREFERRED EMBODIMENTS THEREOF

The present invention provides a method of delivering DFM's to birds so that the DFM's are established in the gastrointestinal tract. *L. reuteri* cells or other DFM's are incorporated onto the surface or within pellets (compacted whey particles). The pellets may be fed to the birds, for example poultry, along with the birds' normal diet.

Lyophilized (freeze-dried) *Lactobacilli reuteri* strains, T-1 (isolated from turkey) and 11284 (isolated from chickens), when held at room temperature (approximately 25° C.) are found to remain viable for as long as 30 days but to decrease in number. For example, a population of $6 \times 10^6$ colony forming units (CFU)/g were recovered of the original $3 \times 10^{10}$ CFU/g at 30 days. It was found that when the lyophilized cells were suspended in an oil, such as sunflower oil at room temperature for 30 days, no loss of viability was observed.

The invention provides in its first embodiment that lyophilized *L. reuteri* cells suspended in oil are coated over pelletized whey particles. Under room temperature, no decrease in viability is observed for up to seven days. When the Lactobacillus coated pelletized particles of whey are mixed with poultry feed, no significant loss of viability occurs over four days at room temperature.

In the second embodiment of the invention *Lactobacillus reuteri* cells in oil are mixed with whey powder and then the mixture is compressed into pellets (compacted whey particles) or tablets. Although survival is lower than in the first embodiment when there is no cooling in the pelletization process, survival is sufficient for use of the pellets (compacted whey particles) as a beneficial food additive which aids in establishing the DFM in the animal.

The features and advantages of the present invention will be more clearly understood by reference to the following examples, which are not to be construed as limiting the invention.

EXAMPLE 1

Powdered whey is exposed to compaction at a pressure of 10–15 lb/in² to form pellets (compacted whey particles). The pellets (compacted whey particles) are milled and sieved to a size which is edible by the birds, for example, −8, +20 mesh for little pellets and −¼", +8 mesh for larger pellets. *Lactobacillus reuteri* strain T-1, 11284 or other strains compatible with the intended host animal species are lyophilized in a cryoprotectant such as milk or whey and then is mixed in an oil, such as a sunflower oil-based drench at a concentration of about $3 \times 10^{10}$/g in the oil. The drench may contain trace amounts of silicon dioxide.

The strains mentioned above have been deposited at the American Type Culture Collection in Rockville, Md.

The pellets (compacted whey particles) of whey are then coated with the Lactobacillus-containing oil which may be done simply by pouring the oil-suspension over the whey pellets (compacted whey particles) so that there are about $5 \times 10^7$ to about $10^8$ cells/g whey. The survival of the Lactobacillus on the pellets (compacted whey particles) is shown in the first column of data in Table 1. The whey particles are then mixed with feed pellets or particles so that the whey particles comprise 2–5% of the feed by weight, so that there are $5 \times 10^5$ to $10^6$ CFU/g feed mix.

TABLE 1

| Time (days) | Oil drench | In Product | Product feed |
| --- | --- | --- | --- |
| 0 | $3 \times 10^{10}$ | $6 \times 10^8$ | $7 \times 10^6$ |
| 1 | ND | $3 \times 10^8$ | $9 \times 10^6$ |
| 2 | ND | $2 \times 10^8$ | $4 \times 10^6$ |
| 3 | $4 \times 10^{10}$ | $6 \times 10^8$ | $7 \times 10^6$ |
| 4 | ND | ND | $4 \times 10^6$ |
| 5 | ND | $3 \times 10^8$ | ND |
| 7 | $3 \times 10^{10}$ | $3 \times 10^8$ | ND |
| 10 | $4 \times 10^{10}$ | ND | ND |
| 20 | $3 \times 10^{10}$ | ND | ND |
| 30 | $3 \times 10^{10}$ | ND | ND |

EXAMPLE 2

A Lactobacillus-oil suspension is prepared as in Example 1. The suspension is then mixed with whey powder in a concentration of $10^7$ per g whey. The mixture is then compacted, milled and sieved as in Example 1. Typical results of survival of the *Lactobacillus reuteri* in such pellets (compacted whey particles) is shown in the central data column of Table 1. The survival when such pellets (compacted whey particles) are mixed with feed as done in Example 1 is shown in the final column of Table 1.

EXAMPLE 3

Turkey poults are fed feed and pellets (compacted whey particles) having about $10^7$ CFU *L. reuteri*/g feed prepared according to Example 2 for a period of 10 days. The total number of lactobacilli found in the bird's cecum is determined for each treatment as colony-forming units per excised and homogenized cecum. Solid Lactobacillus selection medium (1.5% agar) as described in references 2, 5, and 7 is used. The percent of the colonies which were *L. reuteri* is determined as described in international patent application PCT/US88/01423 but using *L. plantarum* as the indicator organism. In this test, colonies of lactobacilli on the LBS agar medium are overlaid with 10 ml of 1% liquified agar containing 0.5M glycerol and a *L. plantarum* inoculum. After anaerobic (GAS-Pack System) incubation at 37° C. for 24 hours, zones of growth inhibition are seen around colonies that produce reuterin from glycerol. These colonies are thus identified and enumerated as *L. reuteri*.

As seen in Table 2, colonization of the ceca by *L. reuteri* is enhanced by the feed treatment as compared to the control. Only ⅕ of the control birds in the results shown are positive for *L. reuteri*, while ⅘ of the treated birds retain significant numbers of *L. reuteri* in the cecum.

TABLE 2

|  | CFU per g Ceca | | % Of Birds |
| --- | --- | --- | --- |
|  | Total Lactobacilli | L. reuteri | Positive For L. reuteri |
| Control birds | $9.0 \times 10^8$ to $1.5 \times 10^{10}$ | $1.5 \times 10^5$ to $1.2 \times 10^8$ | 20% |
| Treated birds | $5.0 \times 10^7$ to $3.7 \times 10^9$ | $4.0 \times 10^7$ to $1.1 \times 10^9$ | 80% |

While the invention has been described with reference to specific embodiments thereof, it will be appreciated that numerous variations, modifications, and embodiments are possible, and accordingly all such variations, modifications, and embodiments are to be regarded as being within the spirit and scope of the invention.

REFERENCES

1. Axelsson L, Lindgren SE. 1987. Characterization and DNA homology of *Lactobacillus reuteri* strains isolated from pig intestine. J. Appl. Bacteriol., 62:433–440.
2. Axelsson L, Chung TC, Dobrogosz WJ, Lindgren SE. 1989. Production of a broad spectrum antimicrobial substance by *Lactobacillus reuteri*. Microbial Ecol. Health Dis., 2:131–136.
3. Bechman TL, Chambers JV, Cunningham MD. 1977. Influence of *Lactobacillus acidophilus* on performance of young diary calves. J. Dairy Sci., 60:74 (abs).
4. Bruce BB, Gilliland SE, Bush LJ, Staley TE. 1979. Influence of feeding cells of *Lactobacillus acidophilus* on the fecal flora of young calves. Oklahoma Anim. Sci. Res. Rep., 207.
5. Chung TC, Axelsson L, Lindgren Se, Dobrogosz WJ. 1989. In vitro studies on reuterin synthesis by *Lactobacillus reuteri*. Microbial Ecol. Health Dis., 2:137–144.
6. Dellaglio F, Arrizza FS, Leda A. 1981. Classification of citrate fermenting lactobacilli isolated from lamb stomach, sheep milk and pecorino romano cheese. Zbl. Bakt. Hyg., Abt. Orig. C2:349–356.
7. Dobrogosz, WJ, Casas IA, Pagano GA, Talarico TL, Sjorberg B-M, Karlson M. 1989. *Lactobacillus reuteri* and the enteric microbiota. In: The Regulatory and Protective Role of the Normal Microflora (Eds: GrubbR, MidtvedtT, NorinE.) Macmillan LTD, London, pp. 283–292.
8. Ellinger DK, Muller LD, Gantz PJ. 1978. Influence of feeding fermented colostrum and *Lactobacillus acidophilus* on fecal flora and selected blood parameters of young dairy calves. J. Dairy Sci., 61:162 (abs).
9. Food and Drug Administration Compliance Policy Guide No. 7126.41, May 2, 1988.
10. Fox SM. 1988. Probiotics: Intestinal inoculants for production animals. Food-Animal Practice, Vet. Med., August issue.
11. Fuller R. 1986. Probiotics. J. Appl. Bacteriol. Symp. Suppl., 1S–7S.
12. Goodenough ER, Kleyn DH. 1976. Influence of viable yoghurt microflora on the digestion of lactose by the rat. J. Dairy Sci., 59:601–606.
13. Hatch RC, Thomas RO, Thayne WV. 1973. Effect of adding *Bacillus acidophilus* to milk fed to baby calves. J. Dairy Sci., 56:682(abs).
14. Kandler O, Stetter K, Kohl R. 1980. *Lactobacillus reuteri* sp. nov. a new species of heterofermentative lactobacilli. Zbl. Bakt. Hyg. Abt. Orig. C1:264–269.
15. Kandler O, Weiss N, 1986. Regular nonsporing Gram positive rods. Bergey's Manual of Systematic Bacteriology (Eds.: Sneath DHA, Mair NC, Sharpe ME, Holt JH), vol. 2:1208–1234. Williams and Wilkins, NY.
16. Metchnikoff E. 1907. Prolongation of Life. Heinemann, London. 17. Morrill JL, Dayton AD, Mickelson R. 1977. Cultured milks and antibiotics for young calves. J. Dairy Sci., 60:1105.
18. Muralidhara KS, Sheggeby GG, Elliker PR, England DC, Sandine WE. 1977. Effects of feeding lactobacilli on the coliform and Lactobacillus flora of intestine tissue and feces from piglets. J. Food Protection, 40:288–295.
19. Orla-Jensen S. 1943. The lactic acid bacteria. Det Kongelige Danske Videnskasbernes Selskab. Biologiske Skrifter, Bind II, Nr. 3. Kobenhavn.
20. Parker RB. 1974. Probiotics, the other half of the antibiotic story. Anim. Nutr. Health. 29:4–8.
21. Parkhurst CR, Edens FW, Casas IA. 1991. *Lactobacillus reuteri* and whey reduce Salmonella colonization in turkey poults. International Poultry Trade Show, Southeastern Poultry and Egg Association, Atlanta, GA., Abs. Sci. Meet., Jan. 30–Feb. 1, 1991.
22. REVUE: Scientifique et Technique, Digestive Microflora and Bioregulation, International Office Of Epizootics, F75017, paris, France, Vol., 8, June, 1989.
23. Sarra PG, Magri M, Bottazzi V, Dellaglio F, Bosi E. 1979. Frequenza di bacilli heterofementanti nelle feci di vitelli lattanti. Arch. Vet. Ital., 30–16–21.
24. Sarra PG, Dellaglio F, Bottazzi V. 1985. Taxonomy of lactobacilli isolated from the alimentary tract of chickens. System. Appl. Microbiol., 6:86–89.
25. Sarra PG, Vescovo M, Fulgoni 1986. Study on crop adhesion genetic determinant in *Lactobacillus reuteri*. Microbiologica, 9:279–285.
26. Sissons JW. 1989. Potential of probiotic organisms to prevent diarrhoea and promote digestion in farm animals—a review. J. Sci. Food Agric., 46:1–13.
27. Speck ML. 1977. Heated yoghurt—is it still yoghurt? J. Food Protection. 40:863–865.
28. Talarico TL, Casas IA, Chung TC, Dobrogosz WJ. 1988. Production and isolation of reuterin: a growth inhibitor produced by *Lactobacillus reuteri*. Antimicrob. Agents. Chemotherap., 32:1854–1858.
29. Talarico TL, Dobrogosz WJ. 1989. Chemical characterization of an antimicrobial substance produced by *Lactobacillus reuteri*. Antimicrob. Agents Chemotherap., 33:674–679.
30. Talarico TL, Dobrogosz WJ. 1990. Purification and characterization of glycerol dehydratase from *Lactobacillus reuteri*. Appl. Environ. Microbiol., 56:1195–1197.
31. Talarico TI, Axelsson L, Novotny J, Fiuzat M, Dobrogosz WJ. 1990. Utilization of glycerol as a hydrogen acceptor by *Lactobacillus reuteri*: Purification of 1,3-propanediol:NAD oxidoreductase. Appl. Environ. Microbiol., 56:943–948.

32. Underdahl NR, Torres-Medina A, Doster AR. 1982. Effect of *Streptococcus faecium* C-68 in control of *Escherichia coli*—induced diarrhoea in gnotobiotic pigs. Amer. J. Vet. Res., 43:2227–2232.
33. Vescovo M, Morelli L, Cocconcelli PS, Bottazzi V. 1984. Protoplast formation, regeneration, and plasmid curing in *Lactobacillus reuteri*. FEMS Microbiol. Lett., 23:333–334.

What is claimed is:

1. A feed additive consisting essentially of powdered whey and a biologically pure culture of lyophilized *Lactobacillus reuteri* cells suspended in oil; wherein said additive is produced by:

a) compacting powered whey at a pressure of 10–15 lb/in$^2$ to produce compacted whey particles; and b) coating said compacted whey particles with a biologically pure culture of lyophilized *Lactobacillus reuteri* cells suspended in oil to produce said feed additive;

and wherein said *Lactobacillus reuteri* cells retain viability for at least four days after being mixed with feed.

2. A method of delivering viable *Lactobacillus reuteri* cells to the gastrointestinal tract of an avian organism, comprising feeding to said avian organism the additive of claim 1.

3. The method of claim 2 wherein said avian organism is a chicken.

4. The method of claim 2 wherein said avian organism is a turkey.

5. A feed additive consisting essentially of powdered whey and a biologically pure culture of lyophilized *Lactobacillus reuteri* cells suspended in oil; wherein said additive is produced by:

a) mixing powdered whey with a biologically pure culture of lyophilized *Lactobacillus reuteri* cells suspended in oil to produce a mixture; and b) compacting said mixture at a pressure of 10–15 lb/in$^2$ to produce said feed additive;

and wherein said *Lactobacillus reuteri* cells retain viability for at least four days after being mixed with feed.

6. A method of delivering viable *Lactobacillus reuteri* cells to the gastrointestinal tract of an avian organism, comprising feeding to said avian organism the additive of claim 5.

7. The method of claim 6 wherein said avian organism is a chicken.

8. The method of claim 6 wherein said avian organism is a turkey.

* * * * *